United States Patent [19]

Descamps et al.

[11] Patent Number: 4,814,485

[45] Date of Patent: Mar. 21, 1989

[54] 4-AMINOBUTANOIC ACID DERIVATIVES, PROCESS OF PREPARATION AND USE THEREOF

[75] Inventors: Marcel Descamps, Wavre, Belgium; Dino Nisato, Saint Georges d'Orques, France; Walter Verstraeten, Mechlin, Belgium

[73] Assignee: Sanofi, France

[21] Appl. No.: 936,777

[22] Filed: Dec. 2, 1986

Related U.S. Application Data

[63] Continuation-in-part of Ser. No. 62,612, Jun. 18, 1986, Pat. No. 4,816,598, which is a continuation of Ser. No. 735,684, May 20, 1985, abandoned.

[30] Foreign Application Priority Data

Dec. 2, 1985 [FR] France ............................. 85 17805

[51] Int. Cl.[4] .......................................... C07C 101/02
[52] U.S. Cl. ...................................... 560/39; 560/12; 560/125; 562/430; 562/444; 562/507
[58] Field of Search ..................... 562/444, 507, 439; 560/39, 12, 125

[56] References Cited

U.S. PATENT DOCUMENTS 3,882,161  5/1975  Eichenberger et at. ............. 562/442
4,240,975 12/1980  Umeyawa et al. .................. 562/444

OTHER PUBLICATIONS

Saino et al, Chem. Abst; vol. 94, #103,789; (1981).
Kirihata et al, Chem. Abst; vol. 96, #143,271g (1982).
Morris, Chem. Abst, vol. 102, #2551d (1985).

Primary Examiner—James H. Reamer
Attorney, Agent, or Firm—Bacon & Thomas

[57] ABSTRACT

The invention relates to new (4S)-4-aminobutanoic acid derivatives of general formula:

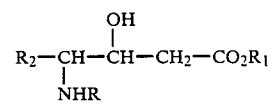

in which:
R represents an N-protective group,
$R_1$ represents hydrogen, an alkali metal atom such as lithium, sodium or potassium or a liabile group,
$R_2$ represents a group of formula:

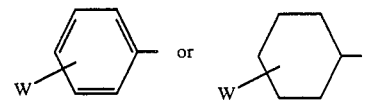

in which W represents hydrogen, a hydroxy group or an alkyl radical containing from 1 to 4 carbon atoms or an alkoxy radical containing from 1 to 4 carbon atoms, and to a process for the preparation of the said derivatives.

The 4-aminobutanoic acid derivatives according to the invention are useful as synthesis intermediates for the preparation of peptides derived from statin analogues.

12 Claims, No Drawings

4-AMINOBUTANOIC ACID DERIVATIVES, PROCESS OF PREPARATION AND USE THEREOF

CROSS REFERENCE TO RELATED APPLICATIONS

This application is a continuation-in-part of co-pending application Ser. No. 62,612 filed June 16, 1986 now U.S. Pat. No. 4,816,598 which is a continuation of application Ser. No. 735,684 filed May 20, 1985 and now abandoned.

The present invention relates to new (4S)-4-aminobutanoic acid derivatives of general formula:

$$R_2-\underset{NHR}{\underset{|}{CH}}-\underset{|}{\overset{OH}{\underset{|}{CH}}}-CH_2-CO_2R_1 \quad I$$

in which:
R represents a N-protective group,
$R_1$ represents hydrogen, an alkali metal atom such as lithium, sodium or potassium or a labile group,
$R_2$ represents a group of formula:

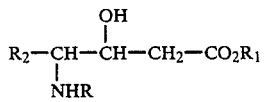

in which W represents hydrogen, a hydroxy group or an alkyl radical containing from 1 to 4 cabon atoms or an alkoxy radical containing from 1 to 4 carbon atoms.

When $R_2$ represents a hydroxyphenyl group, p-hydroxyphenyl forms a preferred group.

In the present context, the terms adopted below carry the following meaning:

"N-protective group" denotes an easily removable group attached to the nitrogen of an amino group such as, for example, a formyl group, an alkylcarbonyl group such as acetyl or propionyl, an alkoxycarbonyl group such as tert-butoxycarbonyl, an alkoxyalkylcarbonyl group such as methoxyacetyl or methoxypropionyl, a substituted alkoxycarbonyl group such as 2,2,2-trichloroethoxycarbonyl, an aralkyloxycarbonyl group such as benzyloxycarbonyl, a substituted aralkyloxycarbonyl group such as p-nitrobenzyloxycarbonyl, a trityl or methoxytrityl group or an arylsulphonyl group such as p-toluenesulphonyl, the tert-butoxycarbonyl (BOC) group forming a preferred group;

"Labile group" denotes an easily removable esterifying group such as an alkyl group containing from 1 to 4 carbon atoms, for example, methyl, ethyl, n-propyl, isopropyl, n-butyl, isobutyl or tert-butyl or a substituted or unsubstituted aralkyl group such as benzyl or xylyl.

Because of the asymmetry of the carbon atoms 3 and 4, the compounds of formula I above may be in the form of diastereoisomers (3S,4S) or (3R,4S).

Consequently, the invention relates to both (3S,4S) and (3R,4S) isomers of the compounds of formula I, in separate forms or in the form of mixtures.

Peptides derived from analogues of (3S,4S)-3-hydroxy-4-amino-6-methylheptanoic acid or statin were described in U.S. Pat. No. 4,485,099 or in European patent application No. 114,993, these peptides being useful for their antihypertensive potentialities by the inhibition of the enzyme which converts renin into angiotensin.

The synthesis of these peptides requires a method for easily obtaining 3-hydroxy-4-amino-6-methylheptanoic acid analogues, especially the (3S,4S) isomers of these analogues.

In the context of the invention, it was found that the N-protected 4-aminobutanoic acid derivatives of the invention are compounds which are especially useful for the preparation of peptides derived from statin analogues, using a process similar to that described in U.S. Pat. No. 4,485,099 or in European patent application No. 114,993.

Peptides prepared from compounds of the invention were found, in fact, to present an inhibitory action on the human plasma renin activity rendering them useful in the treatment of arterial hypertension.

Hence, another object od the invention relates to the use of the compounds of formula I for the preparation of peptides derived from statin analogues.

The N-protected 4-aminobutanoic acid derivatives of the invention may be prepared easily and with a high degree of purity, especially the (3S,4S) isomers, according to a process which can be extrapolated to an industrial-scale production.

According to the invention, N-protected (3S,4S)- and(3R,4S)-3-hydroxy-4-aminobutanoic acid derivatives of formula I are prepared:

(a) When $R_1$ represents a labile group, by the hydrogenation of a protected (4S)-3-oxo-4-aminobutanoic acid derivative of general formula:

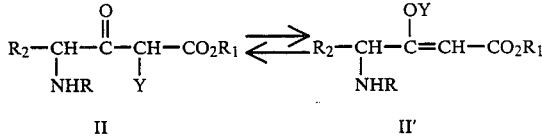

in which R and $R_2$ have the same meaning as above, the hydroxy group which may optionally be present being protected, for example, by a benzyl radical, $R_1$ represents a labile group and Y represents hydrogen or an alkali metal atom, for example, lithium, sodium or potassium and this is carried out in the presence of a catalyst, for example, Raney nickel, at room-temperature in a suitable solvent, for example methanol and, at a pressure, for example, of approximately 7 bars in order to obtain the desired compounds in the form of a mixture of diastereoisomers, (b) When $R_1$ represents an alkali metal atom, by the saponification by means of an alkali metal hydroxide, for example, lithium, sodium or potassium hydroxide, of a protected (3S,4S)- or (3R,4S)-3-hydroxy-4-aminobutanoic acid ester prepared in paragraph (a) above and this is carried out in a suitable solvent such as aqueous dioxan and at room-temperature, in order to obtain the desired compounds in the form of a mixture of diastereoisomers, (c) When $R_1$ represents hydrogen, by the acidification at room-temperature by means of a strong acid such as hydrochloric acid, of a protected (3S, 4S)- or (3R,4S)-3-hydroxy-4-aminobutanoic acid salt prepared in paragraph (b) above, in order to obtain the desired compounds in the form of a mixture of diastereoisomers, it being possible for these diastereoisomers, if desired, to be separated, for example, by chromatography.

The protected (4S)-3-oxo-4-aminobutanoic acid derivatives of formula II-II' may be prepared from a protected amino acid of general formula:

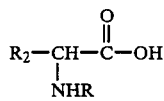

in which R and $R_2$ have the same meaning as in formula II-II', which amino acid can be obtained by protecting by conventional means the amino and hydroxy groups of the corresponding L-amino acid. Such amino acids can be prepared in a way similar to that described in Belgian Pat. No. 845,187.

The protected amino acid of formula III, on reacting with N,N-thionyldiimidazole, according to a method similar to that described in Bull. Soc. Chim. France, 1964, pp. 945–951, produces the protected imidazolide of general formula:

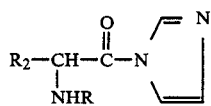

in which R and $R_2$ have the same meaning as in formula II-II'.

This imidazolide of formula IV is then reacted with a magnesium enolate of a malonic acid monoester of general formula:

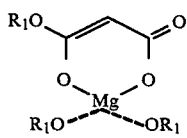

in which $R_1$ has the same meaning as above, the reaction being carried out at room-temperature and in an ether such as tetrahydrofuran, if required, in the presence of a polar aprotic solvent such as dimethylsulphoxide or N,N-dimethylformamide to give a complex which is hydrolyzed in the presence of a strong acid, for example, hydrochloric acid, in order to thereby give esters of protected (4S)-3-oxo-4-aminobutanoic acid derivatives of formula II-II' in which Y represents hydrogen.

Such an ether/polar aprotic solvent mixture is generally recommended: for the preparation of the esters of formula II-II' under consideration.

In this case, a tetrahydrofuran/dimethylsulphoxide mixture is preferably used, which enables high yields of the desired product to be obtained in a pure form whereas in tetrahydrofuran alone, the yields are generally lower.

The alkali metal salt of the esters of formula II-II', in which Y represents an alkali metal atom, are then formed by reacting the butanoate derivatives of formula II-II', in which Y represents hydrogen, the reaction being carried out in an aqueous medium containing, if required, an organic solvent such as hexane, with an alkali metal hydroxide, for example, lithium, sodium or potassium hydroxide and at a temperature less than 20° C., and the salt formed is then separated from the reaction medium.

The alkali metal salts thus obtained may be used especially for the regeneration of esters of formula II-II' in which Y represents hydrogen and this is carried out by the acidification of their aqueous solution by means of a strong acid, for example, hydrochloric acid.

In this application, the intermediate isolation of the alkali metal salts in question is a choice method for the purification of the esters of formula II-II' in which Y represents hydrogen, obtained in the crude state during the implementation of the preparation process described above.

This purification passing through the corresponding alkali metal salt enables the esters of formula II-II', in which Y represents hydrogen, to be obtained with high yields.

The esters of formula II-II' in which Y represents hydrogen thus purified may therefore subsequently be reduced with catalytic hydrogen to give the corresponding esters of formula I in the form of a mixture of diastereoisomers.

At this stage, it is possible to carry out the separation of the two diastereoisomers, for example, by chromatography.

Additionally, it was observed that the preparation of the esters of formula I may be carried out directly using salts of formula II-II' by the catalytic reduction of these compounds with hydrogen. In this way, one stage in the process, viz. the regeneration of the esters of formula II-II', in which Y represents hydrogen, is avoided, after purification by the intermediate passage through the alkali metal salt.

The compounds of formula I can be used for preparing peptides in accordance with the usual methods of peptide chemistry. In particular, they can be prepared by a stepwise process from the terminal C.

The starting material is a compound of formula I in ester form with which the next aminoacid is condensed.

After the amine group of the dipeptide has been freed, the peptide chain is lengthened by coupling with the next aminoacid, suitably protected. Each coupling stage is followed by a selective operation for freeing the amine which will react to create the next peptide linkage. The various coupling operations are carried out either using an activated ester of the aminoacid to be coupled or using the N-protected aminoacid itself, in the presence of dicyclohexylcarbodiimide.

The stages of selective freeing of the amine are carried out either by hydrogenolysis or by acidolysis in a strong acid medium such as trifluoroacetic acid, depending on the nature of the protecting group used.

Finally, if the aminoacid which is to be introduced into the sequence possesses, in its side chain, a functional group capable of reacting (this is the case of histidine in particular), the functional group should be blocked by a suitable protecting group, which is subsequently removed.

Finally the peptide in the acid form can be obtained from the corresponding esters by saponification in a dilute alkaline medium.

The following non-limiting examples illustrate the preparation of the compounds of the invention together with the use of such compounds.

In all these examples, the following abbreviations will be used:

Aminoacids and protecting or activating groups (a) Aminoacids
- Ala — Alanine
- Nle — Norleucine
- Sta — Statin (3S,4S) configuration
- Phe — Phenylalanine (b) Protecting and activating groups
- APHBA — (3S,4S)-3-hydroxy-4-amino-4-phenylbutanoic acid
- BOC — t-Butoxycarbonyl
- ONP — p-Nitrophenyl ester  ONSU — N—Hydroxysuccinimide ester The following abbreviations will also be used:

- BOP — Benzotriazolyloxy-tris-dimethylaminophosphonium hexafluorophosphate
- HOBt — p-Hydroxybenzotriazole
- H.P.L.C. — High pressure liquid chromatography
- Phe — Phenylalanine  NEM — N—Ethylmorpholine
- M.P. — Melting point
- N.M.R. — Nuclear magnetic resonance
- T.L.C. — Thin layer chromatography.

PREPARATIONS

(A) N,N'-thionyldiimidazole

In a one-liter round-bottomed flask equipped with a stirrer and a separating funnel closed with a guard tube filled with a desiccant were placed 13.6 g (0.2 mol) of imidazole dissolved in 150 ml of tetrahydrofuran.

A solution of 6 g of thionyl chloride in 50 ml of tetrahydrofuran was then added, with stirring.

The precipitation of imidazole hydrochloride started immediately.

After stirring for 20 minutes, the contents were filtered and the precipitate was washed with 50 ml of tetrahydrofuran. A clear solution of N,N'-thionyldiimidazole was thereby obtained, which was used as such in the following operation.

(B) Imidazolide of 2-(N-BOC-amino)-2-phenylacetic acid in L form

The solution obtained as above was placed in a one-liter round-bottomed flask equipped with a stirrer and a separating funnel an a solution of 12.5 g (0.05 mol) of 2-(N-BOC-amino)-2-phenylacetic acid in the L form in 20 ml of tetrahydrofuran was then added dropwise.

The stirring was continued for 20 minutes, evacuating the sulphur dioxide formed by suction under reduced pressure (approximately 2660 Pa). A slightly turbid solution of the imidazolide of 2-(N-BOC-amino)-2-phenylacetic acid in the L form was thereby obtained, which was used as such.

(C) Methyl hydrogen malonate

In a 4-liter round-bottomed flask, equipped with a stirrer and a separating funnel were placed 660 g (5 mols) of dimethyl malonate. A solution at 20° C. of 281 g of potassium hydroxide in 2 liters of methanol was then added in the course of approximately 8 hours.

After stirring for 15 to 16 hours at room-temperature, the precipitate of the potassium salt of methyl hydrogen malonate was filtered and carefully washed with ethyl ether.

The precipitate was taken up in 750 ml of water and acidified to a pH of 2 to 3 with dilute hydrochloric acid, cooling with an ice/methanol mixture at the same time. Extraction was carried out 3 times with ethyl ether, the ether phase was dried and evaporated to dryness.

In this manner 156 g of crude methyl hydrogen malonate were obtained which represent a yield of 26%.

After a distillation under $5.10^{-2}$ Torr at 80°–85° C., 135 g of pure product were isolated which represents a yield of 23%.

$n_D^{23} = 1.4300$.

N.M.R.: in agreement.

Protometric assay: 97.17%.

(D) Magnesium enolate of methyl hydrogen malonate

Into a 2-liter round-bottomed flask, equipped with a stirrer, a condenser and a separating funnel were successively introduced 4.8 g (0.2 mol) of magnesium, 0.2 ml of carbon tetrachloride and 10 ml of methanol.

Under stirring, 10 ml of a solution of 23.5 g (0.2 mol) of methyl hydrogen malonate in 50 ml of methanol were added to this mixture.

The reaction started spontaneously. When it became less violent, the remaining malonate solution was added so as to maintain a slight reflux. When the addition was complete, the flask was heated in a water bath for 8 hours. After this operation, 200 ml of tetrahydrofuran were added and the heating in the water bath was continued for 12 hours. The solvents were then distilled, first at atmospheric pressure and then at approximately 2660 Pa. On reaching dryness, 100 ml of benzene were added and the contents were distilled at atmospheric pressure and then under vacuum. Finally, 100 ml of tetrahydrofuran were added.

A suspension of magnesium enolate of methyl hydrogen malonate was thereby obtained.

EXAMPLE 1

Preparation of methyl (3S,4S)- and (3R,4S)-3-hydroxy-4-(N-BOC-amino)-4-phenylbutanoate.

I. Sodium salt of methyl (4S)-3-oxo-4-(N-BOC-amino)-4-phenylbutanoate

The imidazolide of 2-(N-BOC-amino)-2-phenylacetic acid in the L form was prepared from 13.6 g of imidazole and 12.5 g of 2-(N-BOC-amino)-2-phenylacetic acid in the L form according to the method described in paragraph B above. Similarly, the magnesium enolate of methyl hydrogen malonate was prepared from 24.7 g of methyl hydrogen malonate according to the method described in paragraph D above.

The imidazolide solution was added to the suspension of magnesium enolate in tetrahydrofuran, and 130 ml of dimethylsulphoxide were then added. The mixture became clear and all the constituents dissolved.

After stirring for 4 hours at room-temperature, the mixture was acidified to neutral pH with 1N hydrochloric acid. The mixture was then stirred for 30 minutes at room-temperature in order to complete the hydrolysis.

Decantation was carried out followed by extraction which was undertaken 3 times with ethyl ether. The ether phase was washed successively with water, bicarbonate water and then with water. After drying over sodium sulphate, the extract was evaporated to dryness and 12.2 g of crude methyl (4S)-3-oxo-4-(N-BOC-amino)-4-phenylbutanoate were obtained.

The crude methyl butanoate derivative was taken up in 60 ml of hexane and 20 ml of water. The heterogenous mixture was stirred and 10 ml of a 30%-strength sodium hydroxide solution was added, at a temperature less than 20° C. The precipitation of the sodium salt started after approximately 5 minutes and the stirring was continued for 15 minutes in order to complete the precipitation.

The precipitate was filtered and it was washed with ice-cold water and with ethyl ether. After drying, the sodium salt of methyl (4S)-3-oxo-4-(N-BOC-amino)-4-phenylbutanoate, slightly soluble in ethyl ether, was obtained.

M.P.: 182°–184° C.

II. Methyl (3S,4S)- and (3R,4S)-3-hydroxy-4(N-BOC-amino)-4-phenylbutanoate

In 150 ml of methanol were dissolved 6 g of sodium salt of methyl (4S)-3-oxo-4-(N-BOC-amino)-4-phenylbutanoate. After adding 1 g of Raney nickel, hydrogenatin was carried out at a pressure of 7 bars for 24 hours.

The alkalinity was neutralized with acetic acid and the mixture was filtered. After evaporation, the residue was taken up with hexane in order to remove inorganic salts and the hexane was then evaporated.

A crude mixture of two diastereoisomers, methyl (3S,4S)- and (3R,4S)-3-hydroxy-4-(N-BOC-amino)-4-phenylbutanoate was thereby obtained.

This crude mixture was then separated by chromatography on a silica column (diameter: 90 mm, height: 500 mm) using a 10:90 mixture of ethyl acetate:hexane.

After evaporation of the different fractions, the two diastereoisomers which crystallized on standing were isolated.

The following products were thereby obtained:

(a) Methyl (3S,4S)-3-hydroxy-4-(N-BOC-amino)-4-phenylbutanoate
M.P.: 94°–95° C. (diisopropyl ether).
$\alpha_D^{25} = +7.9°$ (C=1, methanol).

(b) Methyl (3R,4S)-3-hydroxy-4-(N-BOC-amino)-4-phenylbutanoate
M.P.: 94°–95° C. (diisopropyl ether).
$\alpha_D^{25} = +1.8°$ (C=1, methanol).

EXAMPLE 2

Preparation of methyl (3S,4S)- and (3R,4S)-3-hydroxy-4-(N-BOC-amino )-4 phenylbutanoate

I. Methyl (4S)-3-oxo-4-(N-BOC-amino)-4-phenylbutanoate

The imidazolide of 2-(N-BOC-amino)-2-phenylacetic acid in the L form was prepared from 136 g of imidazole and 125 g of 2-(N-BOC-amino)-2-phenylacetic acid in the L form according to the method described in paragraph B above. Similarly, magnesium enolate of methyl hydrogen malonate was prepared from 236 g of methyl hydrogen malonate according to the method described in paragraph D above.

The imidazolide solution was added to the magnesium enolate suspension in tetrahydrofuran and 1.3 liter of dimethylsulphoxide was then added. The mixture became clear and all the constituents dissolved.

After stirring for 4 hours at room-temperature, the mixture was acidified to neutral pH with 1N hydrochloric acid and stirring was carried out for 30 minutes at room-temperature in order to complete the hydrolysis.

Decantation was carried out followed by extraction with ethyl ether 3 times. The ether phase was washed successively with water, bicarbonate water and then water. After drying over sodium sulphate, the extract was evaporated to dryness and crude methyl (4S)-3-oxo-4-(N-BOC-amino)-4-phenylbutanoate was obtained.

The crude methyl butanoate derivative was taken up in 200 ml of isopropyl ether, 200 ml of hexane and 100 ml of water.

While stirring 50 ml of 30%-strength sodium hydroxide were then added at a temperature less than 20° C. After stirring for 15 minutes, the precipitate of the sodium salt of methyl (4S)-3-oxo-4-(N-BOC-amino)-4-phenylbutanoate formed was filtered and washed with hexane. The wet precipitate was taken up with a water/hexane mixture and 1N hydrochloric acid was added until pH=2 to 3.

Extraction was carried out twice with hexane and the organic phase was washed with a 10%-strength sodium bicarbonate solution. After drying and evaporation, 80 g of methyl (4S)-3-oxo-4-(N-BOC-amino)-4-phenylbutanoate in an oily form were isolated.

Yield: 52% calculated on the basis of the starting 2-(N-BOC-amino)-2-phenylacetic acid in the L form.
$\alpha_D^{25} = +77°$ (C=1, methanol).
M.P.: 97°–98° C.
N.M.R. and T.L.C.: in agreement.

II. Methyl (3S,4S)- and (3R,4S)-3-hydroxy-4-(N-BOC-amino)-4-phenylbutanoate

In 400 ml of anhydrous methanol were dissolved 80 g of pure methyl (4S)-3-oxo-4(N-BOC-amino)-4-phenylbutanoate obtained from its sodium salt. After the addition of approximately 6 g of Raney nickel, hydrogenation was carried out for 72 hours at a pressure of approximately 7 bars and at a temperature of approximately 20° C.

After this operation, filtration was carried out followed by evaporation to dryness in order to obtain a mixture of two diastereoisomers:methyl (3S,4S)- and (3R,4S)-3-hydroxy-4-(N-BOC-amino)-4-phenylbutanoate in an oily form.

This oil was then separated by chromatography on a silica gel column (diameter: 90 mm, height: 500 mm) using a 10:90 mixture of ethyl acetate:hexane.

After evaporating the different fractions, the two diastereoisomers which crystallized on standing were isolated.

The following were thereby obtained:

(a) Methyl (3S,4S)-3-hydroxy-4-(N-BOC-amino)-4-phenylbutanoate
Yield: 12% calculated on the basis of the 3-oxo derivative.
M.P.: 94°–95° C. (diisopropyl ether).
$\alpha_D^{25} = +7.9°$ (C=1, methanol).

(b) Methyl (3R,4S)-3-hydroxy-4-(N-BOC-amino)-4-phenylbutanoate
Yield: 45% calculated on the basis of the 3-oxo derivative.
M.P.: 94°–95° C. (diisopropyl ether).
$\alpha_D^{25} = +1.8°$ (C=1, methanol).

The following Example illustrates the preparation of a peptide from a comPound of formula I.

EXAMPLE I

Preparation of BOC-Phe-Nle-APHBA-Ala-Sta-OCH₃ (SR 44205)

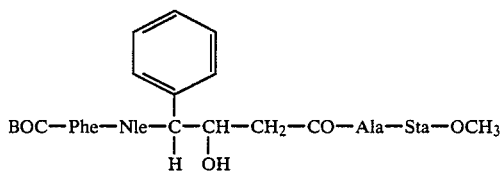

(a) Methyl-4-(N-BOC-norleucylamino)-3-hydroxy-4-phenylbutanoate

In 10 ml of pure trifluoroacetic acid was dissolved at 0° C. 1 g (0.0032 mol) of methyl (3S,4S)-3-hydroxy-4-(N-BOC-amino)-4-phenylbutanoate partially in racemic form. After 15 min. at 0° C., the acid was rapidly evaporated off under reduced pressure wlthout heatlng. Then the vapor had disappeared, the salt so obtained was suspended in methylene chloride at 0° C. and therewere successively added 1.06 g (0.0032 mol) of BOC-Nle-ObSU, 0.620 g (0.004 mol) of HOBt and then a sufficient amount of NEM to bring the pH of the solution to 6–7. The reaction medium was heated to room-temperature in 2 h, while controling the pH, and then stirred for 12 to 15 h. The solvent was evaporated off at room-temperature using a Büchi evaporator and the peptide was extracted by means of ethyl acetate. The organic phase was then washed with 4 fractions of a dilute aqueous solution of sodium carbonate, 2 fractions of water, 4 fractions of a dilute aqueous solution of potassium hydrogenosulphate then with 2 fractions of water and only one fraction of an aqueous solution of sodium chloride. The medium was dried on magnesium sulphate and purified by chromatography on silicagel while eluting with a 1/1 mixture of methylene chloride/ethyl acetate. After triturating in an ethyl ether/hexane mixture, 0.629 g of methyl 4-(N-BOC-norleucylamino)-3-hydroxy-4-phenylbutanoate was obtained.

(b) Methyl 4-(N-BOC-phenylalanyl-norleucylamino)-3-hydroxy-4-phenylbutanoate.

In 5 ml of trifluoroacetic acid, 0.453 g (1.07×10⁻³ mol) of methyl 4-(N-BOC-norleucylamino)-3-hydroxy-4-phenylbutanoate previously obtained was triturated at 0° C. After 15 min. of contact, the acid in excess was evaporated off at room-temperature using a BHchi evaporator. The salt so obtained was dissolved in 10 ml of methylene chloride at 0° C. and there were successively added 0.498 g (1.2 equivalent) of BOC-Phe-ONP and 0.197 g (1.2 equivalent) of HOBt. The reaction medium was neutralized with N-methylmorpholine and then allowed to return to room-temperature while adjusting the pH at about 7 with a supplemental amount of N-methylmorpholine.

The medium was evaporated to dryness and an aqueous solution of sodium carbonate was added. After extraction with 3 volumes of ethyl acetate, the extract was washed with an aqueous solution of sodium carbonate, with water and then with an aqueous solution of sodium chloride. After drying on magnesium sulphate and evaporation of the solvent under vacuum, the residue was chromatographed on a silicagel column while eluting with a 50/50 v/v mixture of methylene chloride/ethyl acetate. After triturating in hexane 0.324 g of methyl 4-(N-BOC-phenylalanyl-norleucylamino)-3-hydroxy-4-phenylbutanoate was obtained in the form of a 80/20 mixture of two isomers detected by H.P.L.C.

(c) BOC-Phe-Nle-APHBA-Ala-Sta-OCH₃

Using a methanol/water/sodium hydroxide mixture was hydrolysed 0.260 g of methyl 4-(N-BOC-phenylalanyl-norleucylamino)-3-hydroxy-4-phenylbutanoate previously obtained. After this operation, trifluoroacetic acid, Ala-Sta-OCH₃ (Prepared from 0.004 g or 1.2 equivalent of BOC-Ala-Sta-OCH₃), 0.210 g of BOP and the acid previously obtained, were mixed in methylene chloride. The medium was neutralized with diisopropylethylamine and stirred at roomtemperature for 15 h. After evaporation of the solvent and extraction with ethylacetate, the extract was concentrated and the residue was twice chromatographed on a silicagel column using a 95/5 v/v mixture of ethyacetate/methanol as eulent. The fractions which appeared to be homogeneous in T.L.C were collected and evaporated and the residue obtained was triturated in ethyl ether.

In this manner BOC-Phe-Nle-APHBA-Ala-Sta-OCH₃ was obtained in a yield of 91% (determined by H.P.L.C.)

M.P.: 214°–216° C.

The impure fractions could be 3 times recrystallized from warm acetonitrile.

Yield: 100% (determined by H.P.L.C.).

M.P.: 214°–216° C.

The peptide so obtained was studied for determining its inhibitory action on the human plasma renin activity using the method described in European patent application No. 104,964.

In accordance with this test, SR 44205 was found to present an IC$_{50}$ of $10^{-6}$M at pH=6, IC$_{50}$ representing the dose of compound under study which causes 50% inhibition of the human plasma renin activity serving as the reference.

We claim:

1. A (4S)-4aminobutanoic acid derivative having a formula:

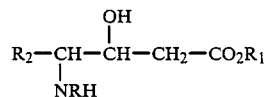

in which:

R represents an N-protective group selected from the group consisting of formyl, alkylcarbonyl, alkoxycarbonyl, alkoxyalkylcarbonyl, substituted alkoxycarbonyl, aralkyloxycarbonyl, substituted aralkyloxycarbonyl, methoxytrityl and arylsulphonyl;

R₁ is hydrogen, an alkali metal atom; a labile group which is an alkyl group containing from 1 to 4 carbon atoms, aralkyl or substituted aralkyl;

R₂ represents a group of the formula:

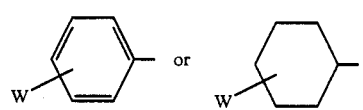

in which W is hydrogen, hydroxy, alkyl containing from 1 to 4 carbon atoms and alkoxy containing from 1 to 4 carbon atoms.

2. A (4S)-4-aminobutanoic acid derivative having a formula:

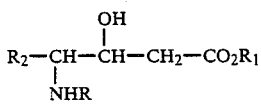

in which:
R represents an N-protective group selected from the group consisting of formyl, acetyl, propionyl, tert-butoxycarbonyl, methoxyacetyl, methyoxypropionyal, 2,2,2-trichloroethoxycarbonyl, benzyloxycarbonyl, p-nitrobenzyloxycarbnonyl, trityl, methoxytrityl and p-toluenesulphonyl;
$R_1$ is hydrogen, an alkali metal atom, or a labile group which is methyl, ethyl, n-propyl, isopropyl, n-butyl, isobutyl, tert-butyl, benzyl or xylyl;
$R_2$ represents a group of formula:

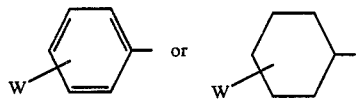

in which W is selected from the group consisting of hydrogen, hydroxy, alkyl containing from 1 to 4 carbon atoms and alkoxy containing from 1 to 4 carbon atoms.

3. 4-Aminobutanoic acid derivatives according to claim 2, of formula I in which $R_2$ represents a phenyl radical.

4. 4-Aminobutanoic acid derivatives according to claim 2, of formula I in which $R_2$ represents a 4-hydroxyphenyl radical.

5. 4-Aminobutanoic acid derivatives according to claim 2, of formula I in which R represents a tert-butoxycarbonyl radical.

6. 4-Aminobutanoic acid derivaties according to claim 2, of formula I in which $R_1$ represents a methyl group.

7. 4-Aminobutanoic acid derivatives according to claim 1, of formula I in which $R_2$ represents a phenyl radical.

8. 4-Aminobutanoic acid derivatives according to claim 1, of formula I in which $R_2$ represents a 4-hydroxyphenyl radical.

9. 4-Aminobutanoic acid derivatives according to claim 1, of formula I in which R represents a tert-butoxycarbonyl radical.

10. 4-Aminobutanoic acid derivatives according to claim 1, of formula I in which $R_1$ represents a methyl group.

11. Methyl (3S,4S)-3-hydroxy-4-(N-BOC-amino)-4-phenylbutanoate.

12. Methyl (3R,4S)-3-hydroxy-4-(N-BOC-amino)-4-phenylbutanoate.

* * * * *